United States Patent [19]

Yamada

[11] Patent Number: 5,416,538
[45] Date of Patent: May 16, 1995

[54] OBJECT-SURFACE-SHAPE MEASURING APPARATUS

[75] Inventor: Kenji Yamada, Yachiyo, Japan

[73] Assignee: Nikon Corporation, Tokyo, Japan

[21] Appl. No.: 143,690

[22] Filed: Oct. 27, 1993

[30] Foreign Application Priority Data

Oct. 29, 1992 [JP] Japan ................................. 4-291020

[51] Int. Cl.6 .................................................. A61B 3/10
[52] U.S. Cl. ..................................... 351/212; 351/247; 356/376
[58] Field of Search ............... 351/212, 247, 221, 205, 351/210, 211; 356/376, 124

[56] References Cited

U.S. PATENT DOCUMENTS

| 3,969,019 | 7/1976 | Nohda | 351/13 |
| 4,439,025 | 3/1984 | Smirmaul | 351/212 |
| 4,511,227 | 4/1985 | Nunokawa et al. | 351/208 |
| 4,768,875 | 9/1988 | Muller | 351/212 |
| 4,787,743 | 11/1988 | Nohda | 351/212 |
| 5,307,151 | 4/1994 | Hof et al. | 356/376 |

FOREIGN PATENT DOCUMENTS

| 1434261 | 1/1967 | France . |
| 1572786 | 11/1967 | Germany . |
| 2516281 | 4/1975 | Germany . |
| 3138122 | 9/1981 | Germany . |
| 3230401 | 8/1982 | Germany . |
| 3536513 | 10/1985 | Germany . |
| 251497 | 7/1986 | Germany . |
| 3933994 | 10/1989 | Germany . |
| 4027328A1 | 8/1990 | Germany . |
| 4130237A1 | 9/1991 | Germany . |
| 57-197404 | 12/1982 | Japan . |

*Primary Examiner*—William L. Sikes
*Assistant Examiner*—Hung Xuan Dang
*Attorney, Agent, or Firm*—Pennie & Edmonds

[57] ABSTRACT

An apparatus is provided for measuring the shape of a surface of an object in compact size, in easy operability and with improved measurement precision. The apparatus is provided with a measurement relay system and an observation relay system for respectively guiding a reflected image of index on the object surface through an objective lens to re-image it at a certain magnification on a photoelectric converter, a member enclosing the measurement relay system and the observation relay system and disposed between the objective lens and the photoelectric converter, and rotating means for rotating the member such that either the optical axis of the measurement relay system or the optical axis of the observation relay system is made coincident with an optical path between the objective lens and the photoelectric converter.

18 Claims, 4 Drawing Sheets

OBJECT-SURFACE-SHAPE MEASURING APPARATUS

BACKGROUND OF THE INVENTION

1. Field of the Invention

The present invention relates to an apparatus for measuring a shape of an object surface, for example a shape of a corneal surface in an eyeball.

2. Related Background Art

A conventional measuring apparatus for measuring a shape of a corneal surface in an eyeball as an object surface are normally arranged, for example as disclosed in Japanese Laid-open Patent Application No. 57-197404, such that light from a projection optical system projecting an index onto the surface of the cornea, is guided through an objective lens and split into an observation path and a measurement path by an optical splitter such as a beam splitter. There are known some of such measuring apparatus in which the reflected light from the corneal surface is split by the optical splitter into the observation path and the measurement path and in which a photoelectric converter for measurement is used also for observation for positioning of the eyeball as the object.

However, if a measuring apparatus is constructed as described above, i.e., such that the reflected light from the corneal surface is split by the optical splitter into the observation path and the measurement path, the scale of apparatus become large and the structure complex. Further, Japanese Laid-open Patent Application No. 57-197404 discloses another structure in which an eyeball as object is observed through an eyepiece and is guided to a predetermined position, which is complicated in operation.

A further drawback exists in the conventional arrangement in which the optical path is split into two and the photoelectric converter for measurement is also used for observation. In such arrangement, an optical system for measurement is constructed in the same manner as an optical system for observation. Thus, if a corneal image of an eyeball is formed on the photoelectric converter during observation at a magnification suitable for measurement, the magnification will be too high for observation, which limits the observation area to only a part of the eyeball. Therefore positioning of the eyeball is very difficult.

SUMMARY OF THE INVENTION

It is, therefore, an object of the present invention to provide an apparatus for measuring a shape of an object surface with improved measurement precision as being compact in size and easy in operation.

An object-surface-shape measuring apparatus according to the present invention is directed specifically to an apparatus for measuring a shape of a corneal surface in an eyeball as an object surface. The apparatus is provided with an observation optical system for observing the entire eyeball in order to adjust a measuring position of the eyeball and a measurement optical system for measuring the shape of the corneal surface.

In particular, the object-surface-shape measuring apparatus comprises a projection optical system for projecting an index onto an object, a measurement relay system for measuring the shape of the object surface, which is an optical system for guiding a reflected image of the index on the object surface through an objective lens and re-imaging it at a predetermined magnification on a photoelectric converter, an observation relay system for observing a projected position of the index, which is an optical system for guiding the reflected image of the index on the object surface through the objective lens and re-imaging it at a predetermined magnification on the photoelectric converter, and rotating means for supporting and rotating the measurement relay system and the observation relay system.

In the above arrangement, the measurement optical system is composed of the objective lens and the measurement relay system, while the observation optical system is composed of the objective lens and the observation relay system. Particularly, the objective lens is common to the two optical systems in the apparatus.

In a specific example, the projection optical system includes two pairs of projection optical units, which are respectively arranged on two different planes. Each of the two planes is a surface including the optical axis of the objective lens. On either one of these planes, each of the paired projection optical units is arranged on either side of the optical axis of the objective lens.

With the projection optical units arranged as above, there are four index pieces projected onto the object surface. The shape of the object surface is defined by distances between the index pieces, which can be measured by obtaining a curvature of the object surface from a deviation between a measured distance and a reference distance.

Each projection optical unit is composed of a light source for projecting an index piece and a collimator lens for collimating rays from the light source. The projection optical unit may be provided with a mask pattern to change the shape of the index into an arbitrary shape. Using the mask pattern in the projection optical unit, the projection optical system can be comprised of one projection optical unit, because the shape of the object surface can be defined by a strain of an arbitrary shape of the index.

The rotating means supports the measurement relay system and the observation relay system and rotates them by a certain angle. Therefore, in order to rotate the relay systems more easily and to realize miniaturization of apparatus, an effective arrangement is such that the relay systems are fixed to a single member and the member is located between the objective lens and the photoelectric converter.

The rotating means rotates the relay systems or the member to which the relay systems are fixed, such that either the optical axis of the measurement relay system or the optical axis of the observation relay system is made coincident with the optical path between the objective lens and the photoelectric converter. In the conventional arrangement in which the optical splitter splits the optical path into two paths for the measurement optical system and for the observation optical system, a quantity of light to the photoelectric converter is decreased, resulting in increasing measurement errors, while in the above arrangement according to the present invention, the measurement optical system and the observation optical system can use the same optical path without Using the optical splitter, which is effective to utilize the quantity of light without waste.

The member described above is a housing enclosing the measurement relay system and the observation relay system with the optical axis of the measurement relay system being perpendicular to the optical axis of the observation relay system. The positional relation between the measurement relay system and the observation relay system can be arbitrarily Changed by changing the traveling direction of light with a reflection mirror, a prism, or the like.

The measurement relay system is composed of a telecentric aperture stop and a negative lens component, while the observation relay system is composed of a negative lens component and a positive lens component. Particularly, the each relay system is not limited to that for re-imaging a real image, but may be an optical system which receives a virtual image formed by the objective lens and forms a larger image than the image formed by the objective lens alone. The relay systems have a negative refracting power, whereby the entire length of optical system can be made shorter.

Further, the apparatus according to the present invention is provided with a photoelectric converter, for example an image sensor, in place of the eyepiece in order to permit the TV screen or the like to be used as display means. Since the each relay system enlarges the reflected image at the predetermined magnification (a larger object image can be observed), as described above, it is easy for an inspector to observe the object and to adjust the measuring position on the object surface.

Incidentally, a sufficient condition for measurement of the shape of object surface is that only the measurement area on which the index pieces are projected onto the image sensor, which is effective to utilize the image sensor surface and improves the measurement precision. On the other hand, for observation of object for adjusting the measuring position, desired positioning is easy if the entire object including the measurement area is displayed on the TV screen or the like used as a monitor. It is thus preferable that a projection magnification in observation is different from that in measurement. In the present invention, an imaging magnification of the measurement relay system on the image sensor is 1.5 or more times greater than that of the observation relay system.

If a too much time elapsed to change over from the observation relay system to the measurement relay system after the fine positioning in observation, the position could be deviated in measurement, failing to achieve the original purpose of improvement of measurement precision. Therefore, the present invention shortens the change-over time by directly or indirectly rotating the member to which the measurement relay system and the observation relay system are fixed, by a predetermined angle by the rotating means.

The rotating means may be a stepping motor enabling precise control of rotation angle. In particular, the reference position for the member enclosing the measurement relay system and the observation relay system is set by a photo interrupter.

DETAILED DESCRIPTION OF THE PREFERRED EMBODIMENTS

Embodiments of the present invention will be described with reference to FIG. 1 to FIG. 8. In the following embodiments, the object is limited to a cornea in an eyeball to explain examples for measuring the shape of corneal surface.

Figure 1:
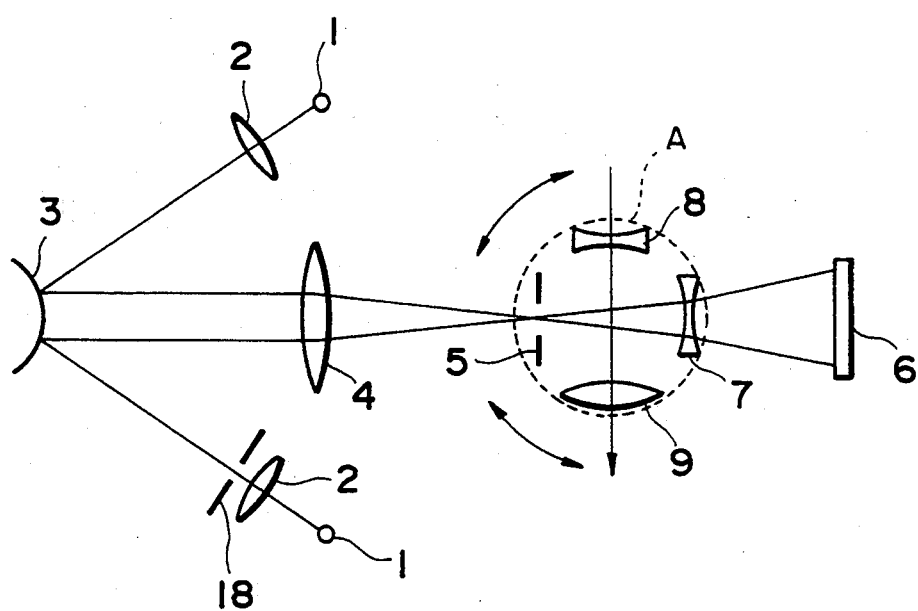
FIG. 1 is a drawing to show a structure of a first embodiment of an object-surface-shape measuring apparatus according to the present invention.

FIG. 1 is a drawing to show a structure of a first embodiment of an object-surface-shape measuring apparatus according to the present invention. The first embodiment is provided with a projection optical system for projecting an index onto the cornea 3, a measurement relay system (composed of a telecentric aperture stop 5 and a negative lens 7) for measuring the shape of the corneal (3) surface, which is an optical system for guiding a reflected image of the index on the cornea 3 through an objective lens 4 and re-imaging it at a predetermined magnification on an image sensor 6 (photoelectric converter), an observation relay system (composed of a negative lens 8 and a positive lens 9) for observing the projected position of the index, which is an optical system for guiding the reflected image of the index on the cornea 3 through the objective lens 4 and re-imaging it at a predetermined magnification on the image sensor 6 used in common with the measurement relay system, and rotating means for rotating the measurement relay system and the observation relay system by a predetermined angle while supporting them.

Although FIG. 1 does not show the rotating means, it may be a stepping motor for example. To facilitate the rotation and to realize miniaturization of this apparatus, which is an object of the invention, an effective arrangement is that the measurement relay system and the observation relay system are fixed to a single member A. A structure of this member A will be detailed later.

The projection optical system is composed of four projection optical units, each of which is composed of a light source 1 for projecting an index piece as shown in FIG. 1 and a collimator lens 2 for collimating rays from the light source 1. The each projection optical unit may have a mask pattern 18 for changing the shape of each index piece into a desired shape. Using the mask pattern 18 in the projection optical unit, the projection optical system is comprised of one projection optical unit, because the shape of the surface of the cornea 3 can be defined by a strain of a desired shape of the index.

In the present embodiment, the projection optical system is composed of two pairs Of projection optical units, which are respectively arranged on two different planes. Each plane is a surface including the optical axis of the objective lens 4. On either one of these planes, each of the paired projection optical units (light source 1 and collimator lens 2) is arranged on either side of the optical axis of objective lens 4.

Figure 2:
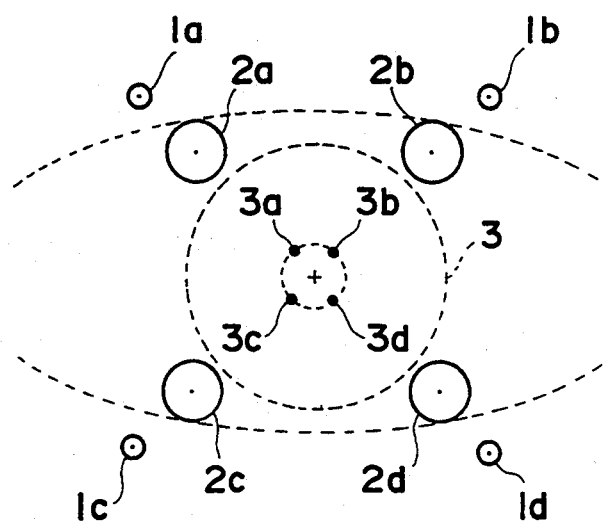
FIG. 2 is a drawing to illustrate an arrangement of projection optical units, which are seen at the position of the objective lens 4 toward the object 3 in FIG. 1.

Using the projection optical system constructed as above, four index pieces are projected onto the surface of the cornea 3. FIG. 2 is a drawing to illustrate this state in detail, which is seen at the position of the objective lens 4 toward the cornea 3 as object.

Accordingly, there are the first projection optical unit (first light source 1a and first collimator lens 2a) and the fourth projection optical unit (fourth light source 1d and fourth collimator lens 2d) located on a same plane. Also, there are the second projection optical unit (second light source 1b and second collimator lens 2b) and the third projection optical unit (third light source 1c and third collimator lens 2c) located on another same plane. Then, the four index pieces 3a to 3d are projected onto the surface of the cornea 3 in actual as shown in FIG. 2. Although FIG. 2 excludes the objective lens 4, it should be understood from the above explanation that the objective lens 4 is located at the center of the drawing.

Figure 3:
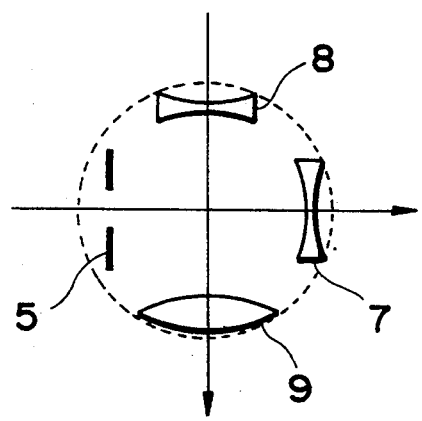
FIG. 3 is a drawing to show a first example of arrangement of a measurement relay system and an observation relay system with a member to which the relay systems are fixed.
Figure 4:
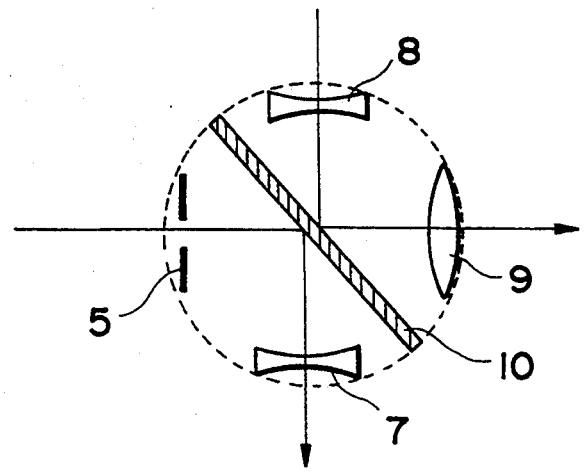
FIG. 4 is a drawing to show a second example of arrangement of a measurement relay system and an observation relay system with a member to which the relay systems are fixed.

Next described with FIG. 3 or FIG. 4 is the construction of the member A to which the measurement relay system and the observation relay system are fixed.

The rotating means rotates the member A such that the optical axis of the measurement relay system becomes coincident with the optical path between the objective lens 4 and the image sensor 6 or that the optical axis of the observation relay system becomes coincident with the optical path between the objective lens 4 and the area image sensor 6.

Accordingly, the measurement relay system is so arranged that when the member A is rotated, the telecentric aperture stop 5 is located on the objective lens (4) side and the negative lens 7 on the image sensor (6) side. Similarly, the observation relay system is so arranged that when the member A is rotated, the negative lens 8 is located on the objective lens (4) side and the positive lens 9 on the image sensor (6) side. The measurement relay system and the observation relay system have the same focal length, so that the in-focus condition is maintained in change-over between the relay systems.

FIG. 3 is a drawing to show a first example of arrangement of the member A, in which the optical axes of the relay systems are perpendicular to each other. Also, FIG. 4 is a drawing to show a second example of arrangement of the member A, in which a reflection mirror 10 is set to change the traveling direction of reflected light in the relay systems.

Figure 5:
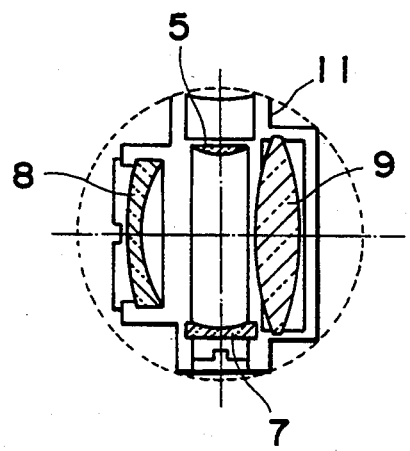
FIG. 5 is a horizontal cross section of the member as shown in FIG. 3.

Further, FIG. 5 is a horizontal cross section to illustrate a specific structure of the member A, in which the relay systems are fixed in a housing 11, realizing the first example of arrangement of the member A. In the first example of the member A, the lens diameter of the observation relay system (negative lens 8 and positive lens 9) is larger, because a wide visual field is preferable in observation, while the lens diameter of the measurement relay system (negative lens 7) is smaller.

In this embodiment, an imaging magnification of the measurement relay system on the image sensor 6 is set 1.5 times greater than that of the observation relay system.

Figure 6:
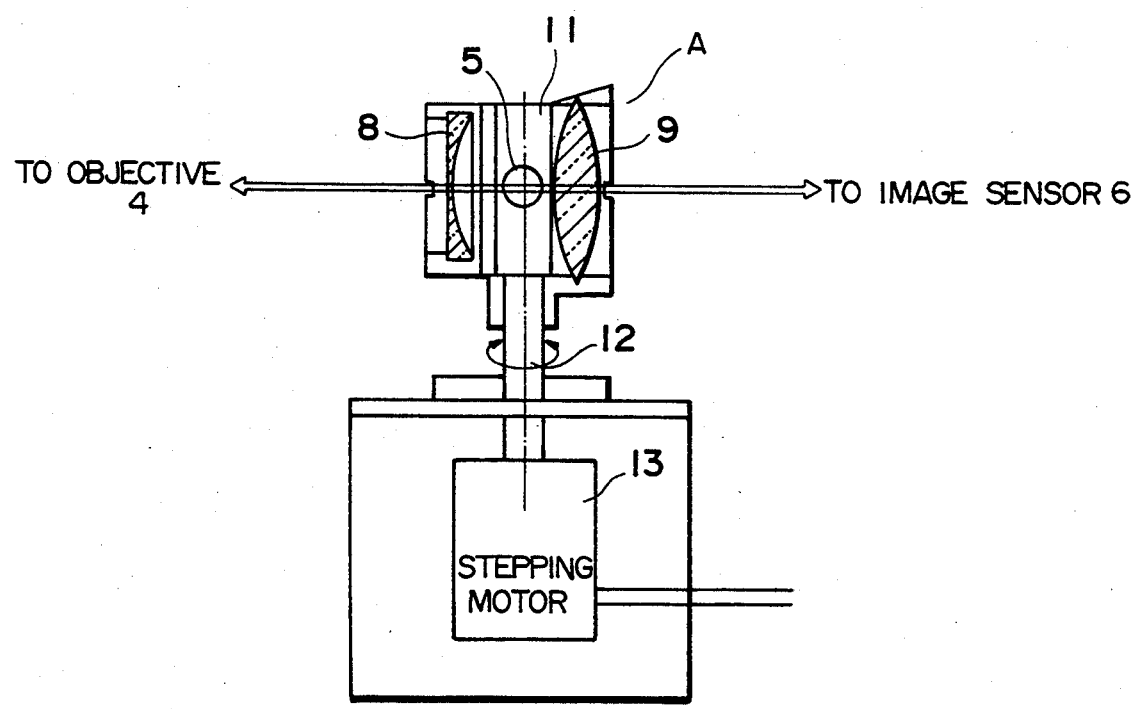
FIG. 6 is a vertical cross section of rotating means.

FIG. 6 is a vertical cross section to show the structure of the rotating means. In this embodiment, a stepping motor 13 enabling precise control of rotation angle is used as the rotating means. The member A is directly connected to the stepping motor 13 through a connecting rod 12, whereby the member A is supported and rotated by the predetermined angle.

Next described is the change-over operation from observation to measurement in the first embodiment of the invention.

First in observation, the entire eyeball is illuminated by an unrepresented light source (different from the light source 1). Rays (reflected image) reflected by the surface of the cornea 3 are guided through the objective lens 4 and the observation relay system (fixed to the member A), in which the negative lens 8 is disposed on the objective lens (4) side and the positive lens 9 is on the image sensor (6) side, to be re-imaged on the image sensor 6. Then the measurement position is adjusted while observing the entire cornea 3 through the TV screen or the like.

In measurement, the stepping motor 13 rotates the connecting rod 12 supporting the member A by 90 degrees thereby to change over from the observation relay system to the measurement relay system.

Since the imaging magnification in measurement on the image sensor 6 is set 1.5 times greater than that in observation, the shape of the corneal (3) surface can be measured more precisely and easily, using data of a larger reflected image (the central region of the cornea 3).

After measurement, the stepping motor 13 again rotates the connecting rod 12 supporting the member A by 90 degrees or 270 degrees thereby to change over from the measurement relay system fixed to the member A to the observation relay system, i.e., to the reference position preliminarily set by a photo interrupter.

Figure 7:
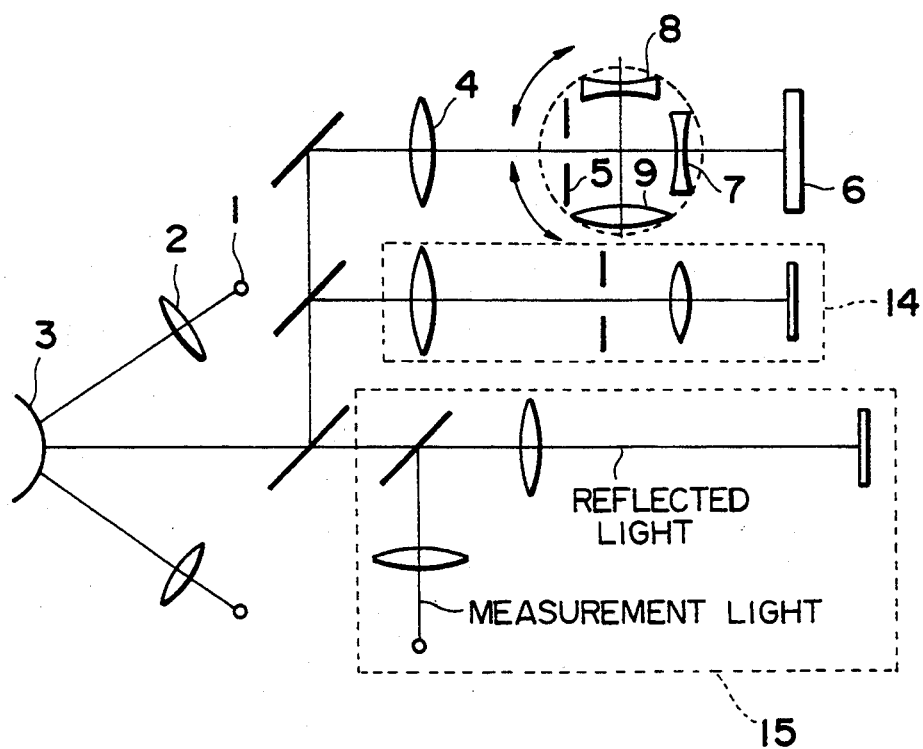
FIG. 7 is a drawing to show, the structure of a second embodiment of an object-surface-shape measuring apparatus according to the present invention.

Next described with FIG. 7 is a second embodiment of the present invention, which is an application example in which the first embodiment (FIG. 1) as described above is combined with a device having another function, for example with a device for measuring an eye refracting power.

As shown in FIG. 7, the second embodiment can measure both an eye refracting power of eye and a shape of a corneal (3) surface, which is very effective in respect of installation space and operability. In FIG. 7, an optical system encircled by the broken line is a fixation system 14 of the cornea 3 as object in the present embodiment. The fixation system 14 is used for fixation of the cornea 3 in measurement of the shape of the corneal (3) surface. In measurement of the eye refracting power, the fixation system 14 is used both for fixation of the eyeball and for release of adjusting power in a device 15 for measuring an eye refracting power. In positioning of the eyeball, measurement light in the device 15 is guided to illuminate the eyeball surface. Using the reflected light from the eyeball surface, positioning of the eyeball can be readily carried out.

Figure 8:
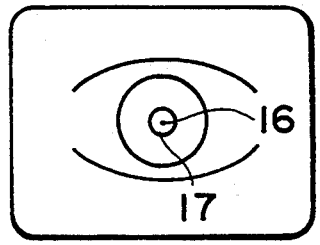
FIG. 8 is a drawing to show:an example of TV screen (monitor) in the second embodiment (in FIG. 7).

FIG. 8 shows a screen of a display device in the second embodiment (as shown in,FIG. 7). In FIG. 8, a reference numeral 16 denotes a reflected light from the eyeball surface illuminated by the measurement light in the device 15 for measuring the eye refracting power, and a reference numeral 17 denotes a target mark for positioning. Since the measurement light in the device 15 is light for illuminating the eye ground, the reflected light in the device 15 does not always have the same focal point as that of the reflected light for measuring the shape of corneal (3) surface. It is thus preferable that the observation relay system and the measurement relay system are preliminarily adjusted taking the focal point difference into consideration.

The present invention permits easier observation of an object as compared with the conventional apparatus.

Also, the present invention can provide the object-surface-shape measuring apparatus which can effect momentary magnification changeover between observation magnification and measurement magnification and which is compact in size and excellent in operability, enabling the measurement of the shape of the object surface at a high measurement precision.

What is claimed is:

1. An object-surface-shape measuring apparatus comprising:
    a projection optical system for projecting an index onto an object;
    a measurement relay system for measuring a shape of a surface of the object, which is an optical system for guiding a reflected image of the index on the surface of the object through an objective lens to re-image the index at a predetermined magnification on a photoelectric converter;
    an observation relay system for observing a projected position of the index, which is an optical system for guiding the reflected image of the index on the surface of the object through the objective lens to re-image the index at a predetermined magnification on the photoelectric converter; and
    rotating means for rotating said measurement relay system and said observation relay system while supporting said relay systems.

2. An object-surface-shape measuring apparatus according to claim 1, wherein
    said projection optical system is composed of two pairs of projection optical units, which are respectively disposed on two different planes including the optical axis of the objective lens, and wherein each of the paired projection optical units is disposed on either side of the optical axis of the objective lens on either one of said two planes.

3. An object-surface-shape measuring apparatus according to claim 2, wherein
    said each projection optical unit is composed of a light source for projecting a piece of the index and a collimator lens for collimating rays from said light source.

4. An object-surface-shape measuring apparatus according to claim 3, wherein
    said projection optical system comprises a mask pattern for providing an index of predetermined shape.

5. An object-surface-shape measuring apparatus according to claim 1, wherein
    said projection optical system is comprised of one projection optical unit, which is comprised of a light source for projecting an index, a collimator lens for collimating rays from said light source, and a mask pattern for providing the index of predetermined shape.

6. An object-surface-shape measuring apparatus according to claim 1, wherein
    said rotating means rotates said measurement relay system and said observation relay system, such that either the optical axis of said measurement relay system or the optical axis of said observation relay system becomes coincident with an optical path between the objective lens and the photoelectric converter.

7. An object-surface-shape measuring apparatus according to claim 6, wherein
    said rotating means comprises a stepping motor for directly or indirectly rotating said measurement relay system and said observation relay system.

8. An object-surface-shape measuring apparatus according to claim 1, wherein
    said measurement relay system and said observation relay system are fixed to a member disposed between the objective lens and the photoelectric converter.

9. An object-surface-shape measuring apparatus according to claim 8, wherein
    said member holds said measurement relay system and said observation relay system, such that the optical axis of said measurement relay system is perpendicular to the optical axis of said observation relay system.

10. An object-surface-shape measuring apparatus according to claim 9, wherein
    said measurement relay system is composed of a telecentric aperture stop and a negative lens component.

11. An object-surface-shape measuring apparatus according to claim 9, wherein
    said observation relay system is composed of a negative lens component and a positive lens component.

12. An object-surface-shape measuring apparatus according to claim 8, wherein
    said member is provided with a reflection mirror for changing a traveling direction of reflected light in said measurement relay system and a traveling direction of reflected light in said observation relay system.

13. An object-surface-shape measuring apparatus according to claim 12, wherein
    said measurement relay system is composed of a telecentric aperture stop and a negative lens component.

14. An object-surface-shape measuring apparatus according to claim 12, wherein
    said observation relay system is composed of a negative lens component and a positive lens component.

15. An object-surface-shape measuring apparatus according to claim 8, wherein
    said rotating means rotates said member to which said measuring relay system and said observation relay system are fixed, such that either the optical axis of said measurement relay system or the optical axis of said observation relay system becomes coincident with an optical path between the objective lens and the photoelectric converter.

16. An object-surface-shape measuring apparatus according to claim 15, wherein
    said rotating means comprises a stepping motor for directly or indirectly rotating the member to which said measurement relay system and said observation relay system are fixed.

17. An object-surface-shape measuring apparatus according to claim 1, wherein
    an imaging magnification of said measurement relay system on the photoelectric converter is 1.5 or more times greater than an imaging magnification of said observation relay system on the photoelectric converter.

18. An object-surface-shape measuring apparatus comprising:
    a projection optical system for projecting an index onto a surface of a cornea in an eyeball;

a measurement relay system for measuring a shape of the surface of the cornea, which is an optical system for guiding a reflected image of the index on the surface of the cornea through an objective lens to re-image the index at a predetermined magnification on a photoelectric converter;

an observation relay system for observing a projected position of the index, which is an optical system for guiding the reflected image of the index on the surface of the cornea through the objective lens to re-image the index at a predetermined magnification on the photoelectric converter; and rotating means for rotating said measurement relay system and said observation relay system while supporting said relay systems.

* * * * *